(12) United States Patent
He et al.

(10) Patent No.: US 10,350,198 B2
(45) Date of Patent: Jul. 16, 2019

(54) PHARMACEUTICAL COMPOSITION OF MEK INHIBITOR AND PREPARATION METHOD THEREOF

(71) Applicant: Chia Tai Tianqing Pharmaceutical Group Co., Ltd., Lianyungang (CN)

(72) Inventors: Xiongxiong He, Lianyungang (CN); Ping Dong, Lianyungang (CN); Jiahui Cai, Lianyungang (CN); Xifeng Lu, Lianyungang (CN); Jiao Xu, Lianyungang (CN); Bo Jiang, Lianyungang (CN); Zhenxue Deng, Lianyungang (CN); Shanshan Sui, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 15/577,227

(22) PCT Filed: May 27, 2016

(86) PCT No.: PCT/CN2016/083613
§ 371 (c)(1),
(2) Date: Nov. 27, 2017

(87) PCT Pub. No.: WO2016/188472
PCT Pub. Date: Dec. 1, 2016

(65) Prior Publication Data
US 2018/0147192 A1    May 31, 2018

(30) Foreign Application Priority Data
May 28, 2015 (CN) .......................... 2015 1 0283950

(51) Int. Cl.
*A61K 31/4355*    (2006.01)
*A61K 9/48*    (2006.01)
*A61P 35/00*    (2006.01)
*A61K 9/20*    (2006.01)
*C07D 491/048*    (2006.01)

(52) U.S. Cl.
CPC ........ *A61K 31/4355* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/48* (2013.01); *A61K 9/4833* (2013.01); *A61K 9/4858* (2013.01); *A61K 9/4866* (2013.01); *A61P 35/00* (2018.01); *C07D 491/048* (2013.01)

(58) Field of Classification Search
CPC .... A61K 31/4355; A61K 9/2027; A61K 9/20; A61K 9/14; A61P 35/00
See application file for complete search history.

(56) References Cited

U.S. PATENT DOCUMENTS
2014/0080804 A1    3/2014    Xiao et al.

FOREIGN PATENT DOCUMENTS

| CN | 102020651 A | | 4/2011 |
|---|---|---|---|
| CN | 102020657 | * | 4/2011 |
| EP | 3178821 A1 | | 6/2017 |
| WO | 102020651 | * | 4/2011 |

OTHER PUBLICATIONS

International Search Report in PCT/CN2016/083613, dated Sep. 1, 2016.

* cited by examiner

*Primary Examiner* — Carlos A Azpuru
(74) *Attorney, Agent, or Firm* — Kilpatrick Townsend & Stockton LLP

(57) ABSTRACT

The present application provides a pharmaceutical composition comprising 6-(2-chloro-4-iodophenylamino)-N-(2-hydroxyethoxy)-5-methyl-4-oxo-4,5-dihydrofuro[3,2-c] pyridine-7-carboxamide or a pharmaceutically acceptable salt, a binder, a surface stabilizer and a dispersant, wherein the pharmaceutical composition can be dispersed in water to form a pharmaceutical suspension having a median particle size, X50, of 0.5 μm to 4.0 μm. Also disclosed are a preparation method thereof and the use thereof for treating cancers.

19 Claims, No Drawings

PHARMACEUTICAL COMPOSITION OF MEK INHIBITOR AND PREPARATION METHOD THEREOF

CROSS-REFERENCE TO RELATED APPLICATION

The present application is a U.S. National Phase of PCT/CN2016/083613, filed May 27, 2016, which claims the priority of Chinese Patent Application No. 201510283950.4, filed with the State Intellectual Property Office of the People's Republic of China on May 28, 2015, the contents of which are incorporated herein by reference in its entirety.

TECHNICAL FIELD

The present application relates to the field of pharmaceutical chemistry, in particular, to a pharmaceutical composition of a MEK inhibitor and a preparation method thereof.

BACKGROUND

Cell signal transduction pathways play important roles in cell growth, proliferation and differentiation. The Ras/Raf/MEK/ERK pathway is a primary signal transduction pathway, which transmits signals from multiple cell surface receptors to transcription factors that regulate gene expression in the cell nucleus. It has been found that abnormal activation of the Ras/Raf/MEK/ERK pathway is often observed in malignant transformed cells, and accordingly it is believed that inhibition of the pathway is beneficial for treating hyperproliferative diseases. MEK is a key member in this pathway as it is downstream of Ras and Raf. In addition, since currently known substrates of MEK phosphorylation are merely MAP kinases, ERK1 and ERK2, MEK is an attractive therapeutic target. Several studies have found that inhibition of MEK has potential therapeutic benefits.

Chinese Patent Application No. CN102020651A discloses a compound of formula I, of which the chemical name is 6-(2-chloro-4-iodophenylamino)-N-(2-hydroxyethoxy)-5-methyl-4-oxo-4,5-dihydrofuro[3,2-c]pyridine-7-carboxamide. The compound is a MEK kinase inhibitor, and can be used for the treatment and/or prophylaxis of proliferative diseases, such as inflammatory diseases or tumors, in particular, melanoma.

Formula I

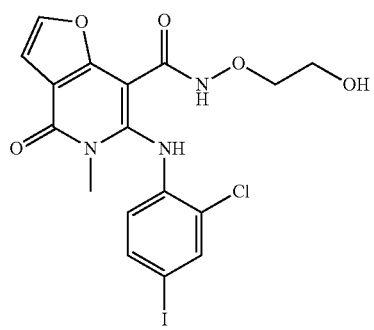

Since the compound of formula I has a low solubility and a low dissolution rate, it difficultly dissolves out after being formulated into a preparation, resulting in its poor drugability. In order to solve the above-mentioned problem, an active compound is usually transformed into a salt form. For example, Selumetinib, a compound structurally similar to the compound of formula I, has a structure as shown in formula II, and its preparation is disclosed in Chinese patent application CN102046156A.

Formula II

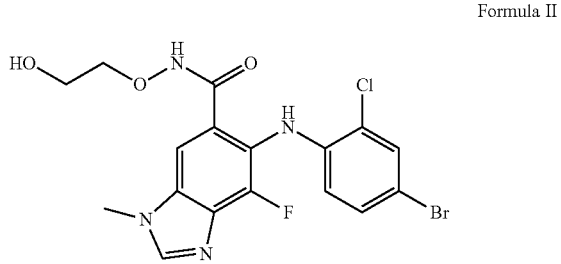 [SMILES: Cn1cnc2c(F)c(Nc3ccc(Br)cc3Cl)c(C(=O)NOCCO)cc21]

However, such compounds have weaker alkalinity. After being transformed into a salt, they are particularly susceptible to dissociation into their free base forms during preparation processing (especially industrial production) and/or storage, thereby reducing their bioavailability and affecting their therapeutic effect. Therefore, such compounds need a complex preparation process and excipients to prepare a formulation, but the final result is not satisfactory.

Accordingly, there is a continuing need for a pharmaceutical composition capable of improving the dissolution and bioavailability of the compound of formula I.

SUMMARY

In one aspect, the present application provides a pharmaceutical composition comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, a binder, a surface stabilizer and a dispersant, wherein the pharmaceutical composition can be dispersed in water to form a pharmaceutical suspension having a median particle size, X50, of 0.5 μm-4.0 μm.

In another aspect, the present application provides a method for preparing a pharmaceutical composition comprising:
1) dissolving a binder and a surface stabilizer in water, adding 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof and uniformly dispersing it;
2) homogenizing the suspension prepared in step 1) at a high pressure;
3) adding a dispersant to the suspension prepared in step 2), stirring, and sieving to remove large particles.

In yet another aspect, the present application provides a use of a pharmaceutical composition comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, a binder, a surface stabilizer and a dispersant, or powders, granules, tablets, pills or capsules comprising the pharmaceutical composition, in the preparation of a medicament for the treatment of a cancer.

In still another aspect, the present application provides a method for treating a cancer, comprising administering to a subject in need thereof a pharmaceutical composition comprising 6-(2-chloro-4-iodophenylamino)-N-(2-hydroxyethoxy)-5-methyl-4-oxo-4,5-dihydrofuro[3,2-c]pyridine-7- carboxamide or a pharmaceutically acceptable salt thereof, a binder, a surface stabilizer and a dispersant, or powders, granules, tablets, pills or capsules comprising the pharmaceutical composition.

In still another aspect, the present application provides a pharmaceutical composition comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, a binder, a surface stabilizer and a dispersant, or powders, granules, tablets, pills or capsules comprising the pharmaceutical composition for the treatment of a cancer.

DETAILED DESCRIPTION

In the following description, certain specific details are included to provide a thorough understanding of various disclosed embodiments. However, those skilled in the relevant art will recognize that the embodiments may be practiced with other methods, components, materials, and the like, instead of one or more of these specific details.

Unless the context requires otherwise, throughout the specification and claims thereafter, the term "comprise" and English variations thereof, such as "comprises" and "comprising", are to be construed in an open and inclusive sense, i.e., "including, but not limited to".

Reference throughout this specification to "one embodiment", or "an embodiment", or "another embodiment", or "some embodiments" means that the particular referent element, structure, or characteristic described in connection with the embodiment is included in at least one embodiment. Accordingly, the appearances of the phases "in one embodiment", or "in an embodiment", or "in another embodiment", or "in some embodiments" in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a", "an" and "the" include plural referents unless the content clearly dictates otherwise. Thus, for example, reference to a reaction in which "a catalyst" is involved includes a single catalyst, or two or more catalysts. Unless otherwise explicitly specified herein, it should also be noted that the term "or" is generally employed in its sense including "and/or".

In one aspect, the present application provides a pharmaceutical composition comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, a binder, a surface stabilizer and a dispersant, wherein the pharmaceutical composition can be dispersed in water to form a pharmaceutical suspension having a median particle size, X50, of 0.5 µm-4.0 µm.

In some embodiments of the present application, the binder is selected from the group consisting of starch paste, methylcellulose (MC), hydroxypropylcellulose (HPC), hydroxypropyl methylcellulose (HPMC), sodium carboxymethylcellulose (CMC-Na), ethylcellulose (EC), polyvinylpyrrolidone (PVP), polyethylene glycol (PEG), and any mixture thereof, preferably hydroxypropylcellulose (HPC), hydroxypropyl methylcellulose (HPMC) or polyvinylpyrrolidone (PVP), and more preferably hydroxypropylcellulose (HPC).

In some embodiments of the present application, the surface stabilizer is selected from the group consisting of sodium dodecyl sulfate, glycerol, syrup, a water-soluble macromolecule compound, and any mixture thereof, preferably sodium dodecyl sulfate or a water-soluble macromolecule compound, and more preferably sodium dodecyl sulfate. The water-soluble macromolecule compound may be selected from the group consisting of acacia, tragacanth, peach gum, methylcellulose (MC), sodium carboxymethylcellulose (CMC-Na), hydroxypropylcellulose (HPC), hydroxypropyl methylcellulose (HPMC), carbopols, polyvinylpyrrolidone (PVP), and dextran, preferably hydroxypropylcellulose (HPC) or hydroxypropyl methylcellulose (HPMC), and more preferably hydroxypropylcellulose (HPC).

In some embodiments of the present application, the dispersant is selected from the group consisting of sucrose, maltose, fructose, glucose, lactose, glycerol, sorbose, xylitol, mannitol, stevioside, saccharin sodium, aspartame, and any mixture thereof, preferably sucrose, fructose or glucose, and more preferably sucrose.

In some embodiments of the present application, the pharmaceutical composition can be dispersed in water to form a pharmaceutical suspension having a median particle size, X50, of 1.0 µm-3.0 µm.

In some embodiments of the present application, the pharmaceutical composition may further comprise blank cores, which are selected from the group consisting of microcrystalline cellulose cores, amylose cores, and lactose cores, preferably microcrystalline cellulose cores and lactose cores.

In some embodiments of the present application, the blank cores may account for 60 wt %-98 wt %, preferably 80 wt %-96 wt %, and more preferably 90 wt %-96 wt %, of the total mass of the pharmaceutical composition.

In some embodiments of the present application, the compound of formula I or a pharmaceutically acceptable salt thereof may account for 0.5 wt %-15 wt %, preferably 0.9 wt %-10 wt %, and more preferably 0.9 wt %-5 wt %, of the total mass of the pharmaceutical composition.

In some embodiments of the present application, the binder may account for 0.25 wt %-15 wt %, preferably 0.5 wt %-5 wt %, and more preferably 0.5 wt %-2.5 wt %, of the total mass of the pharmaceutical composition.

In some embodiments of the present application, the surface stabilizer may account for 0.02 wt %-15 wt %, preferably 0.05 wt %-5 wt %, and more preferably 0.1 wt %-3.5 wt %, of the total mass of the pharmaceutical composition.

In some embodiments of the present application, the dispersant may account for 0.5 wt %-30 wt %, preferably 1 wt %-15 wt %, and more preferably 2 wt %-10 wt %, of the total mass of the pharmaceutical composition.

In respect of the pharmaceutical composition comprising blank cores of the present application, an outer layer containing 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, a binder, a surface stabilizer and a dispersant may surround the blank core, and is optionally further surrounded by a coating. The coating may comprise a film-forming agent and/or a plasticizer and/or a pigment. The film-forming agent may be selected from the group consisting of hydroxypropylcellulose, hydroxypropyl methylcellulose, polyvinylpyrrolidone, sodium carboxymethylcellulose, methylcellulose, and any mixture thereof. The plasticizer may be selected from the group consisting of triethyl citrate, tributyl citrate, glycerol triacetate, polyethylene glycol, and any mixture thereof. The pigment may be selected from the group consisting of titanium dioxide, iron oxide yellow, iron oxide red, and any mixture thereof.

When the pharmaceutical composition comprising blank cores of the present application is dispersed in water, the blank cores are dissolved or deposited at the bottom of the resulting pharmaceutical suspension. Accordingly, the pharmaceutical suspension described in the present application does not comprise the blank cores, and furthermore, the median particle size of the pharmaceutical suspension does not involve the blank cores.

In some embodiments of the present application, the pharmaceutical composition of the present application may be in the form of pellets, preferably pellets having a particle size of 0.2 mm-1.2 mm, and more preferably pellets having a particle size of 0.5 mm-0.8 mm.

In some embodiments of the present application, the pharmaceutical composition of the present application may be pellets, each of which comprises a blank core and an outer layer surrounding the blank core and comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, a binder, a surface stabilizer and a dispersant.

In some embodiments of the present application, the pharmaceutical composition of the present application may be pellets comprising a blank core and an outer layer surrounding the blank core and comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, a binder, a surface stabilizer and a dispersant, wherein the blank core is a microcrystalline cellulose core or a lactose core; the binder is selected from the group consisting of hydroxypropylcellulose (HPC), hydroxypropyl methylcellulose (HPMC), polyvinylpyrrolidone (PVP), and any mixture thereof; the surface stabilizer is selected from the group consisting of sodium dodecyl sulfate, a water-soluble macromolecule compound, and any mixture thereof; and the dispersant is selected from the group consisting of sucrose, fructose, glucose, and any mixture thereof.

In some embodiments of the present application, the pharmaceutical composition of the present application may be pellets comprising a microcrystalline cellulose blank core and an outer layer surrounding the microcrystalline cellulose blank core and comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, hydroxypropyl cellulose, sodium dodecyl sulfate, and sucrose.

In some embodiments of the present application, the pharmaceutical composition may be optionally blended with other pharmaceutically acceptable excipients to formulate into powders, granules, tablets, pills or capsules.

In some embodiments of the present application, other pharmaceutically acceptable excipients include, but are not limited to, a filler, a disintegrant, a lubricant, an adhesive, a plasticizer, a film coating premix, and a capsule shell.

In some embodiments of the present application, the filler may be selected from the group consisting of microcrystalline cellulose, starch, pregelatinized starch, lactose, sucrose, glucose, mannitol, xylitol, sorbitol, and any mixture thereof, preferably microcrystalline cellulose and/or lactose, and more preferably microcrystalline cellulose.

In some embodiments of the present application, the disintegrant may be selected from the group consisting of dry starch, sodium carboxymethyl starch (CMS-Na), low substituted hydroxypropyl methylcellulose (L-HPC), cros-carmellose sodium (CCNa), cross-linked polyvinylpyrrolidone (PVPP), and any mixture thereof, preferably croscarmellose sodium (CCNa) and/or cross-linked polyvinylpyrrolidone (PVPP), and more preferably croscarmellose sodium (CCNa).

In some embodiments of the present application, the lubricant may be selected from the group consisting of magnesium stearate, colloidal silicon dioxide, talc powder, and any mixture thereof, preferably magnesium stearate.

In some embodiments of the present application, the adhesive blended with the pharmaceutical composition may be selected from the group consisting of starch paste, methylcellulose (MC), hydroxypropylcellulose (HPC), hydroxypropyl methylcellulose (HPMC), sodium carboxymethylcellulose (CMC-Na), ethylcellulose (EC), polyvinylpyrrolidone (PVP), polyethylene glycol (PEG), and any mixture thereof, preferably hydroxypropylcellulose (HPC), hydroxypropyl methylcellulose (HPMC) or polyvinylpyrrolidone (PVP), and more preferably hydroxypropylcellulose (HPC).

In some embodiments of the present application, the plasticizer may be selected from the group consisting of polyethylene glycol, triethyl citrate, diethyl phthalate (DEP), dimethyl phthalate (DMP), dibutyl phthalate (DBP), and any mixture thereof, preferably polyethylene glycol and/or triethyl citrate, and more preferably polyethylene glycol.

In some embodiments of the present application, the capsule shell may be selected from a vegetarian capsule shell or a gelatin capsule shell.

In another aspect, the present application provides a method for preparing the pharmaceutical composition, comprising:

1) dissolving a binder and a surface stabilizer in water, adding 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, and then uniformly dispersing it;

2) homogenizing the suspension prepared in step 1) at a high pressure;

3) adding a dispersant to the suspension prepared in step 2), stirring, and sieving to remove large particles.

In some embodiments of the present application, conditions for the high-pressure homogenization in step 2) are 600-3000 bar and 1-15 cycles, preferably 600-2000 bar and 2-8 cycles, and more preferably 800-1500 bar and 5-8 cycles.

In some embodiments of the present application, in step 3), after the addition of the dispersant and stirring, the resulting mixture is passed through a 40 mesh sieve.

In some embodiments of the present application, the method for preparing the pharmaceutical composition may further comprise a step 4): applying the pharmaceutical suspension prepared in step 3) onto blank cores.

In some embodiments of the present application, the pharmaceutical suspension prepared in step 3) is sprayed onto the blank cores in a fluidized bed, i.e. fluidized coating.

In some embodiments of the present application, the blank cores are selected from the group consisting of microcrystalline cellulose cores, amylose cores, and lactose cores, preferably microcrystalline cellulose cores and lactose cores.

In some embodiments of the present application, a pharmaceutical composition comprising a compound of formula I or a pharmaceutically acceptable salt thereof, a binder, a surface stabilizer and a dispersant may be further filled into a capsule shell. In some embodiments of the present application, a pharmaceutical composition comprising a compound of formula I or a pharmaceutically acceptable salt thereof, a binder, a surface stabilizer and a dispersant may be optionally further blended with a filler, a disintegrant, a lubricant, an adhesive, a plasticizer and/or a film coating premix to formulate into powders, granules, tablets or pills.

As used herein, the term "fluidized coating" refers to a method for applying a suspension onto the surface of solid particles in a fluidized bed.

In yet another aspect, the present application provides a use of a pharmaceutical composition comprising a compound of formula I or a pharmaceutically acceptable salt thereof, a binder, a surface stabilizer and a dispersant, or powders, granules, tablets, pills or capsules comprising the pharmaceutical composition in the preparation of a medicament for the treatment of a cancer. The cancer is preferably melanoma.

In still another aspect, the present application provides a method for treating a cancer, comprising administering to a subject in need thereof a pharmaceutical composition comprising a compound of formula I or a pharmaceutically acceptable salt thereof, a binder, a surface stabilizer and a dispersant, or powders, granules, tablets, pills or capsules comprising the pharmaceutical composition. The cancer is preferably melanoma.

In still another aspect, the present application provides a pharmaceutical composition comprising a compound of formula I or a pharmaceutically acceptable salt thereof, a binder, a surface stabilizer and a dispersant, or powders, granules, tablets, pills or capsules comprising the pharmaceutical composition for the treatment of a cancer. The cancer is preferably melanoma.

In some embodiments of the present application, a pharmaceutical composition comprising a compound of formula I or a pharmaceutically acceptable salt thereof, a binder, a surface stabilizer and a dispersant, or powders, granules, tablets, pills or capsules comprising the pharmaceutical composition are orally administered.

The pharmaceutical composition comprising a compound of formula I or a pharmaceutically acceptable salt thereof, a binder, a surface stabilizer and a dispersant provided by the present application has good redispersibility, and can be rapidly dispersed in water to form a pharmaceutical suspension having a median particle size, X50, of 0.5 μm-4.0 μm. The pharmaceutical composition comprising a compound of formula I or a pharmaceutically acceptable salt thereof, a binder, a surface stabilizer and a dispersant, or the powders, granules, tablets, pills or capsules comprising the pharmaceutical composition provided by the present application have a good dissolution effect, thereby improving the bioavailability of the compounds of formula I. The preparation process provided by the present application can greatly reduce the dust of the compound of formula I or a pharmaceutically acceptable salt thereof in the production environment, highly reduce the mucosal irritation to an operator, have a higher safety, and accordingly be suitable for industrial production. Furthermore, the pharmaceutical composition prepared by the preparation process has a narrow particle size distribution and a good uniformity.

EXAMPLES

The present invention will now be described in further detail with reference to specific examples. However, these examples are only for illustrative purposes, and not intended to limit the scope of the present invention.

Example 1: Preparation of Capsules Comprising the Compound of Formula I

Formula

| Components | Every 1,000 capsules |
| --- | --- |
| Compound of formula I | 4 g |
| Hydroxypropylcellulose (HPC) SL | 2 g |
| Sodium dodecyl sulfate | 0.5 g |
| Sucrose | 8 g |
| Microcrystalline cellulose cores (0.5-0.7 mm) | 280 g |

Preparation Process:

1) weighing the formulated amount of hydroxypropylcellulose (HPC) SL, adding water and stirring until dissolved, and thereby obtaining a 4% (W/W) aqueous solution; then adding the formulated amount of sodium dodecyl sulfate and dissolving it; and adding the compound of formula I under stirring and uniformly dispersing it;

2) homogenizing the suspension obtained in step 1) for 5 cycles at a homogenization pressure of 800 bar;

3) adding the formulated amount of sucrose to the suspension obtained in step 2), stirring until dissolved, and passing the suspension through a 40 mesh sieve;

4) fluidized-coating the pharmaceutical suspension obtained in step 3) onto microcrystalline cellulose cores in a fluidized bed at an atomization pressure of 1.5 bar-2.5 bar and a material temperature of 38° C.-45° C. to obtain drug-containing pellets;

5) mixing all the drug-containing pellets obtained in step 4) for 3 minutes at a rate of 10 rpm;

6) measuring the content of the compound of formula I in the product obtained in step 5), and filling the product into capsules according to the measured content.

Example 2: Preparation of Capsules Comprising the Compound of Formula I

Formula

| Components | Every 1,000 capsules |
| --- | --- |
| Compound of formula I | 4 g |
| Hydroxypropylcellulose (HPC) SL | 2 g |
| Sodium dodecyl sulfate | 0.5 g |
| Sucrose | 8 g |
| Microcrystalline cellulose cores (0.5-0.7 mm) | 280 g |

Preparation Process:

1) weighing the formulated amount of hydroxypropylcellulose (HPC) SL, adding water and stirring until dissolved, and thereby obtaining a 4% (W/W) aqueous solution; then adding the formulated amount of sodium dodecyl sulfate and dissolving it; and adding the compound of formula I under stirring and uniformly dispersing it;

2) homogenizing the suspension obtained in step 1) for 8 cycles at a homogenization pressure of 1500 bar;

3) adding the formulated amount of sucrose to the suspension obtained in step 2), stirring until dissolved, and passing the suspension through a 40 mesh sieve;

4) fluidized-coating the pharmaceutical suspension obtained in step 3) onto microcrystalline cellulose cores in a fluidized bed at an atomization pressure of 1.5 bar-2.5 bar and a material temperature of 38° C.-45° C. to obtain drug-containing pellets;

5) mixing all the drug-containing pellets obtained in step 4) for 3 minutes at a rate of 10 rpm;

6) measuring the content of the compound of formula I in the product obtained in step 5), and filling the product into capsules according to the measured content.

Example 3: Preparation of Capsules Comprising the Compound of Formula I

Formula

| Components | Every 1,000 capsules |
| --- | --- |
| Compound of formula I | 4 g |
| Hydroxypropyl methylcellulose (HPMC) E5LV | 1 g |
| Sodium dodecyl sulfate | 0.2 g |
| Saccharin sodium | 4 g |
| Microcrystalline cellulose cores (0.5-0.7 mm) | 50 g |

Preparation Process:

1) weighing the formulated amount of hydroxypropyl methylcellulose (HPMC) E5LV, adding water and stirring until dissolved; then adding the formulated amount of sodium dodecyl sulfate and dissolving it; and adding the compound of formula I under stirring and uniformly dispersing it;

2) homogenizing the suspension obtained in step 1) for 5 cycles at a homogenization pressure of 1000 bar;

3) adding the formulated amount of saccharin sodium to the suspension obtained in step 2), stirring until dissolved, and passing the suspension through a 40 mesh sieve;

4) fluidized-coating the pharmaceutical suspension obtained in step 3) onto microcrystalline cellulose cores in a fluidized bed at an atomization pressure of 1.5 bar-2.5 bar and a material temperature of 38° C.-45° C. to obtain drug-containing pellets;

5) mixing all the drug-containing pellets obtained in step 4) for 3 minutes at a rate of 10 rpm;

6) measuring the content of the compound of formula I in the product obtained in step 5), and filling the product into capsules according to the measured content.

Example 4: Preparation of Capsules Comprising the Compound of Formula I

Formula

| Components | Every 1,000 capsules |
| --- | --- |
| Compound of formula I | 4 g |
| Sodium carboxymethylcellulose | 4 g |
| Sodium dodecyl sulfate | 0.1 g |
| Glucose | 12 g |
| Microcrystalline cellulose cores (0.5-0.7 mm) | 400 g |

Preparation Process:

1) weighing the formulated amount of sodium carboxymethylcellulose, adding water and stirring until dissolved; then adding the formulated amount of sodium dodecyl sulfate and dissolving it; and adding the compound of formula I under stirring and uniformly dispersing it;

2) homogenizing the suspension obtained in step 1) for 4 cycles at a homogenization pressure of 1200 bar;

3) adding the formulated amount of glucose to the suspension obtained in step 2), stirring until dissolved, and passing the suspension through a 40 mesh sieve;

4) fluidized-coating the pharmaceutical suspension obtained in step 3) onto microcrystalline cellulose cores in a fluidized bed at an atomization pressure of 1.5 bar-2.5 bar and a material temperature of 38° C.-45° C. to obtain drug-containing pellets;

5) mixing all the drug-containing pellets obtained in step 4) for 3 minutes at a rate of 10 rpm;

6) measuring the content of the compound of formula I in the product obtained in step 5), and filling the product into capsules according to the measured content.

Example 5: Preparation of Tablets Comprising the Compound of Formula I

Formula

| Components | Every 1,000 tablets |
| --- | --- |
| Compound of formula I | 8 g |
| Polyvinylpyrrolidone (PVP) K30 | 4 g |
| Sodium dodecyl sulfate | 0.1 g |
| Aspartame | 12 g |
| Microcrystalline cellulose | 100 g |
| Lactose monohydrate | 100 g |
| Croscarmellose sodium (CC-Na) | 8 g |
| Magnesium stearate | 1 g |

Preparation Process:

1) weighing the formulated amount of polyvinylpyrrolidone (PVP) K30, adding water and stirring until dissolved; then adding the formulated amount of sodium dodecyl sulfate and dissolving it; and adding the compound of formula I under stirring and uniformly dispersing it;

2) homogenizing the suspension obtained in step 1) for 2 cycles at a homogenization pressure of 1800 bar;

3) adding the formulated amount of aspartame to the suspension obtained in step 2), stirring until dissolved, and passing the suspension through a 40 mesh sieve;

4) immersing the formulated amount of lactose monohydrate particles into the fluidized bed, spraying the pharmaceutical suspension obtained in step 3) onto the lactose monohydrate particles at an atomization pressure of 0.5 bar-1.0 bar and a material temperature of 33° C.-38° C. to obtain drug-containing intermediate A;

5) drying the drug-containing intermediate A obtained in step 4) at an inlet air temperature of 55° C.;

6) adding formulated amounts of microcrystalline cellulose, croscarmellose sodium (CC-Na) and magnesium stearate to the dried drug-containing intermediate A, and mixing uniformly for 10 minutes at a rate of 15 rpm;

7) measuring the content of the compound of formula I in the product obtained in step 6), and tableting the product according to the measured content.

Example 6: Preparation of Tablets Comprising the Compound of Formula I

Formula

| Components | Every 1,000 tablets |
| --- | --- |
| Compound of formula I | 2 g |
| Polyvinylpyrrolidone (PVP) K30 | 1 g |
| Sodium dodecyl sulfate | 0.1 g |
| Sucrose | 4 g |
| Microcrystalline cellulose | 50 g |
| Lactose monohydrate | 150 g |

-continued

| Components | Every 1,000 tablets |
|---|---|
| Croscarmellose sodium (CC-Na) | 6 g |
| Magnesium stearate | 1 g |

Preparation Process:

1) weighing the formulated amount of polyvinylpyrrolidone (PVP) K30, adding water and stirring until dissolved; then adding the formulated amount of sodium dodecyl sulfate and dissolving it; and adding the compound of formula I under stirring and uniformly dispersing it;

2) homogenizing the suspension obtained in step 1) for 3 cycles at a homogenization pressure of 1600 bar;

3) adding the formulated amount of sucrose to the suspension obtained in step 2), stirring until dissolved, and passing the suspension through a 40 mesh sieve;

4) immersing the formulated amount of lactose monohydrate particles into the fluidized bed, spraying the pharmaceutical suspension obtained in step 3) onto the lactose monohydrate particles at an atomization pressure of 0.5 bar-1.0 bar and a material temperature of 33° C.-38° C. to obtain drug-containing intermediate B;

5) drying the drug-containing intermediate B obtained in step 4) at an inlet air temperature of 55° C.;

6) adding formulated amounts of microcrystalline cellulose, croscarmellose sodium (CC-Na) and magnesium stearate to the dried drug-containing intermediate B, and mixing uniformly for 10 minutes at a rate of 15 rpm;

7) measuring the content of the compound of formula I in the product obtained in step 6), and tableting the product according to the measured content.

Reference Example: Preparation of Capsules Comprising the Compound of Formula I

Formula

| Components | Every 1,000 capsules |
|---|---|
| Compound of formula I | 4 g |
| Hydroxypropylcellulose (HPC) SL | 2 g |
| Sodium dodecyl sulfate | 0.5 g |
| Sucrose | 8 g |
| Microcrystalline cellulose cores (0.5-0.7 mm) | 280 g |

Preparation Process:

1) weighing the formulated amount of hydroxypropylcellulose (HPC) SL, adding water and stirring until dissolved, thereby obtaining a 4% (W/W) aqueous solution; then adding the formulated amount of sodium dodecyl sulfate and dissolving it; and adding the compound of formula I under stirring and uniformly dispersing it;

2) adding the formulated amount of sucrose to the suspension obtained in step 1), stirring until dissolved, and passing the suspension through a 40 mesh sieve;

3) fluidized-coating the pharmaceutical suspension obtained in step 2) onto the formulated amount of microcrystalline cellulose cores in a fluidized bed at an atomization pressure of 1.5 bar-2.5 bar and a material temperature of 38° C.-45° C. to obtain drug-containing pellets;

4) mixing all the drug-containing pellets obtained in step 3) for 3 minutes at a rate of 10 rpm;

5) measuring the content of the compound of formula I in the product obtained in step 4), and filling the product into capsules according to the measured content.

Example 8: Re-Dispersion Test

Appropriate amounts of contents in the capsules of Examples 1-4 and Reference example, the drug-containing intermediate A of Example 5 and the drug-containing intermediate B of Example 6 were weighed, all of which correspond to 25 mg of the compound of formula I, and then 50 ml of water was added, shaken until fully dispersed. An upper suspension was carefully taken as a test solution (It should be operated carefully so as not to take undissolved cores), and the test solution was stirred at each measurement. Purified water was used as a blank solution, and an appropriate amount of the suspension was re-dispersed in purified water. A volume/mass distribution particle size was measured by using the laser particle size analyzer.

Instrument: laser diffraction particle size analyzer (HELOS-OASIS, Sympatec, Germany), using SUCELL dispersion system and R1 detection lens (range: 0.1 μm-35 μm);

Ultrasonication time: 300 s;
Stirring speed: 10%;
Acquisition time: 20 s;
Measured concentration: 1%-10%.

| | particle size (μm) | | |
|---|---|---|---|
| | $X_{10}$ | $X_{50}$ | $X_{90}$ |
| Example 1 contents in capsules | 0.76 | 2.84 | 6.45 |
| Example 2 contents in capsules | 0.51 | 1.02 | 3.10 |
| Example 3 contents in capsules | 0.82 | 2.63 | 6.16 |
| Example 4 contents in capsules | 0.76 | 2.78 | 6.24 |
| Example 5 drug-containing intermediate A | 0.62 | 2.68 | 6.29 |
| Example 6 drug-containing intermediate B | 0.58 | 2.57 | 6.14 |
| Reference example contents in capsules | 1.27 | 5.66 | 15.48 |

Example 9: Dissolution Test

The capsules of Examples 1-4 and 7 and the tablets of Examples 5-6 were tested according to the dissolution test (Chinese Pharmacopoeia, 2010 Edition, Part II, Appendix X C, the Second Method). 500 ml of 0.3% sodium dodecyl sulfate (SDS) aqueous solution was used as the dissolution medium, and the rotation speed was 75 rpm. 10 ml samples were taken at 5, 10, 15, 20, 30 and 45 min respectively, and meanwhile equal volumes of the isothermal medium were added. The dissolution solution was filtered with a 0.22 μm polyether sulfone filter, and the subsequent filtrate was taken as a test solution. The absorbance was measured at the wavelength of 324 nm according to the Ultraviolet-Visible spectrophotometry (Chinese Pharmacopoeia, 2010 Edition, Part II, Appendix IV A). About 20 mg of the compound of formula I, which served as a control, was taken and precisely weighed, and thereto 10 ml of DMSO was added, and dissolved under ultrasound. Then, the dissolution medium was added until it reached the neck of the volumetric flask, which was then shaken vigorously. The solution was topped up to volume with dissolution medium and shaken well to prepare a stock solution containing about 200 μg of the compound of formula I per ml. An appropriate amount of the stock solution was taken, and diluted with the dissolution medium to prepare a solution containing about 8 μg of the compound of formula I per ml as a control solution, and its absorbance was measured at the wavelength of 324 nm according to the Ultraviolet-Visible spectrophotometry (Chinese Pharmacopoeia, 2010 Edition, Part II, Appendix IV A). The dissolution curve was calculated based on the absorbance according to the external standard method.

|  | 5 min | 10 min | 15 min | 20 min | 30 min | 45 min |
|---|---|---|---|---|---|---|
| Example 1 capsule | 24.7% | 48.7% | 65.7% | 77.2% | 82.8% | 85.6% |
| Example 2 capsule | 54.5% | 81.5% | 89.8% | 95.1% | 99.4% | 101.1% |
| Example 3 capsule | 24.60% | 51.36% | 68.70% | 80.60% | 84.52% | 87.69% |
| Example 4 capsule | 25.36% | 49.62% | 66.53% | 78.66% | 82.47% | 86.51% |
| Example 5 tablet | 16.31% | 35.68% | 68.92% | 79.63% | 83.16% | 86.92% |
| Example 6 tablet | 14.36% | 33.62% | 69.52% | 81.23% | 84.56% | 87.30% |
| Reference example capsule | 17.1% | 28.8% | 34.4% | 39.0% | 42.7% | 45.2% |

What is claimed is:

1. A pharmaceutical composition, comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, a binder, a surface stabilizer, and a dispersant, wherein the pharmaceutical composition can be dispersed in water to form a pharmaceutical suspension having a median particle size, X50, of 0.5 μm-4.0 μm.

2. The pharmaceutical composition according to claim 1, wherein the binder is selected from the group consisting of starch paste, methylcellulose, hydroxypropyl cellulose, hydroxypropyl methylcellulose, sodium carboxymethylcellulose, ethylcellulose, polyvinylpyrrolidone, polyethylene glycol, and any mixture thereof.

3. The pharmaceutical composition according to claim 1, wherein the surface stabilizer is selected from the group consisting of sodium dodecyl sulfate, glycerol, syrup, a water-soluble macromolecule compound, and any mixture thereof.

4. The pharmaceutical composition according to claim 3, wherein the water-soluble macromolecule compound is selected from the group consisting of acacia, tragacanth, peach gum, methylcellulose, sodium carboxymethylcellulose, hydroxypropylcellulose, carbopols, polyvinylpyrrolidone, dextran, and any mixture thereof.

5. The pharmaceutical composition according to claim 1, wherein the dispersant is selected from the group consisting of sucrose, maltose, fructose, glucose, lactose, glycerol, sorbose, xylitol, mannitol, stevioside, saccharin sodium, aspartame, and any mixture thereof.

6. The pharmaceutical composition according to claim 1, wherein the pharmaceutical composition can be dispersed in water to form the pharmaceutical suspension having a median particle size, X50, of 1.0 μm-3.0 μm.

7. The pharmaceutical composition according to claim 1, wherein the pharmaceutical composition further comprises blank cores, and the blank cores are selected from the group consisting of microcrystalline cellulose cores, amylose cores, and lactose cores.

8. The pharmaceutical composition according to claim 7, wherein the blank cores account for from 60 wt %-98 wt % of the total mass of the pharmaceutical composition.

9. The pharmaceutical composition according to claim 7, wherein the 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof accounts for from 0.5 wt %-15 wt % of the pharmaceutical composition.

10. The pharmaceutical composition according to claim 7, wherein the binder accounts for from 0.25 wt %-15 wt % of the total mass of the pharmaceutical composition.

11. The pharmaceutical composition according to claim 7, wherein the surface stabilizer accounts for from 0.02 wt %-15 wt % of the total mass of the pharmaceutical composition.

12. The pharmaceutical composition according to claim 7, wherein the dispersant accounts for from 0.5 wt %-30 wt % of the total mass of the pharmaceutical composition.

13. The pharmaceutical composition according to claim 7, wherein the pharmaceutical composition is pellets comprising a microcrystalline cellulose core and an outer layer surrounding the microcrystalline cellulose core and comprising 6-(2-chloro-4-iodophenylamino)-N-(2-hydroxyethoxy)-5-methyl-4-oxo-4,5-dihydrofuro[3,2-c]pyridine-7-carboxamide or a pharmaceutically acceptable salt thereof, hydroxypropylcellulose, sodium dodecyl sulfate, and sucrose.

14. The pharmaceutical composition according to claim 13, wherein the outer layer is coated with a coating comprising a film-forming agent and/or a plasticizer and/or a pigment.

15. The pharmaceutical composition according to claim 1, further comprising a filler, a disintegrant, a lubricant, an adhesive, a plasticizer, a film coating premix and/or a capsule shell.

16. The pharmaceutical composition according to claim 15, wherein the pharmaceutical composition is in the form of granules, tablets, pills or capsules.

17. A granule, tablet, pill or capsule comprising the pharmaceutical composition according to claim 1.

18. The pharmaceutical composition according to claim 2, wherein the binder is selected from the group consisting of hydroxypropylcellulose, hydroxypropyl methylcellulose, polyvinylpyrrolidone, and any mixture thereof.

19. The pharmaceutical composition according to claim 3, wherein the surface stabilizer is selected from the group consisting of sodium dodecyl sulfate, a water-soluble macromolecule compound, and any mixture thereof.

* * * * *